United States Patent [19]

Oxford et al.

[11] Patent Number: 5,114,950
[45] Date of Patent: May 19, 1992

[54] 5,6-DIHYDRO-N-[(IMIDAZOL-4(OR 5)-YL)METHYL]-4H-PYRROLO[3,2,1-IJ]QUINOLINE-1-CARBOXAMIDES HAVING 5-HT₃ ANTAGONIST ACTIVITY

[75] Inventors: Alexander W. Oxford, Royston; David E. Bays, Ware; David J. Cavalla, Cambridge; Peter C. North, Royston, all of England

[73] Assignee: Glaxo Group Limited, London, England

[21] Appl. No.: 538,072

[22] Filed: Jun. 13, 1990

[30] Foreign Application Priority Data

Jun. 14, 1989 [GB] United Kingdom ............... 8913646

[51] Int. Cl.⁵ .................... C07D 451/14; A61K 31/44
[52] U.S. Cl. ........................................ 514/294; 546/94
[58] Field of Search ........................ 546/94; 514/294

[56] References Cited

U.S. PATENT DOCUMENTS

| | | | |
|---|---|---|---|
| 4,015,005 | 3/1977 | Goetz | 514/294 |
| 4,151,282 | 4/1979 | Welstead et al. | 514/294 |
| 4,567,177 | 1/1986 | Bigg et al. | 514/214 |
| 4,619,941 | 10/1986 | Wright et al. | 514/397 |
| 4,808,581 | 2/1989 | Oxford et al. | 514/212 |
| 4,963,546 | 10/1990 | North et al. | 514/314 |

FOREIGN PATENT DOCUMENTS

| | | | |
|---|---|---|---|
| 0297651 | 1/1989 | European Pat. Off. | 546/72 |
| 0322016 | 6/1989 | European Pat. Off. | 546/94 |
| 0393766 | 10/1990 | European Pat. Off. | 546/94 |
| 2125398A | 3/1984 | United Kingdom | 546/127 |

Primary Examiner—Alan L. Rotman
Attorney, Agent, or Firm—Bacon & Thomas

[57] ABSTRACT

The invention provides amide derivatives of the general formula (I)

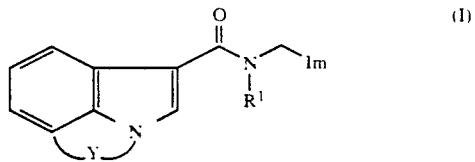

wherein $R^1$ is a hydrogen atom or a $C_{1-6}$alkyl group; Y represents a group $-(CH_2)_m-$, where m represents 2, 3 or 4 or a group $-X(CH_2)_p$, where p represents 2 or 3, X represents an oxygen or a sulphur atom or a group $NR^5$, where $R^5$ is a $C_{1-6}$alkyl group, and X is attached to the benzene ring moiety of the molecule; and Im represents an imidazolyl group of the formula:

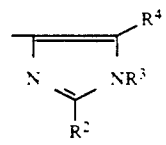

or

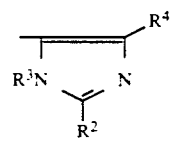

wherein one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group; and physiologically acceptable salts and solvates thereof.

The compounds of formula (I) are potent and selective antagonists of 5-hydroxytryptamine at 5-HT₃ receptors and are useful, for example, in the treatment of psychotic disorders, anxiety and nausea and vomiting.

7 Claims, No Drawings

5,6-DIHYDRO-N-[(IMIDAZOL-4(OR 5)-YL)METHYL]-4H-PYRROLO[3,2,1-IJ]QUINO-LINE-1-CARBOXAMIDES HAVING 5-HT₃ANTAGONIST ACTIVITY

This invention relates to amide derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT₃ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT₃ receptors have been described previously.

Thus for example published European Patent Specification No. 242973 discloses ketone derivatives which may be represented by the general formula:

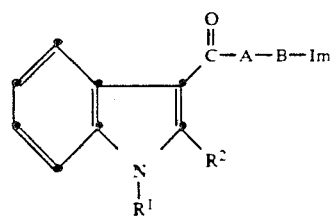

wherein $R^1$ and $R^2$ each represent a hydrogen atom or one of a variety of substituents; A—B represents the group $R^3R^4C$—$CH_2$ or $R^3C$=$CH$; $R^3$ and $R^4$ independently represent a hydrogen atom or a $C_{1-6}$alkyl group; and Im represents an imidazolyl group of formula:

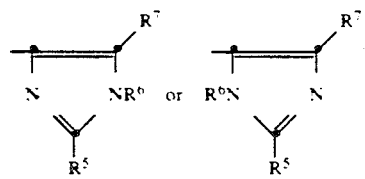

wherein one of the groups represented by $R^5$, $R^6$ and $R^7$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups independently represents a hydrogen atom or a $C_{1-6}$alkyl group.

UK Patent Application No. 2125398A discloses inter alia 5-HT₃ antagonists of formula:

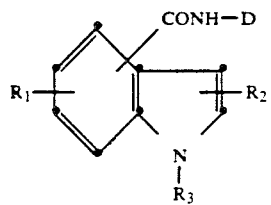

wherein $R_1$, $R_2$ and $R_3$ independently represent a hydrogen atom or one of a variety of substituents; and D represents a group of formula:

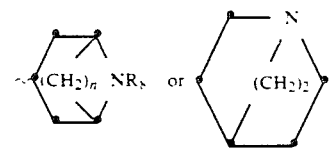

wherein n is 2,3 or 4; and $R_8$ is hydrogen, $C_{1-7}$alkyl, $C_{3-5}$alkenyl or aralkyl.

European Patent Specification No. 297651 discloses annelated derivatives of the compounds described in UK Patent Application No. 2153821, both groups of compounds being antagonists of 5-HT at 5-HT₃ receptors. The compounds of EP-A-297651 may be represented by the general formula:

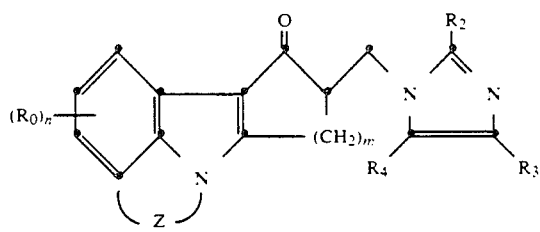

wherein $R_0$ is one of a variety of substituents; n is 0, 1 or 2; Z together with the carbon atom and nitrogen atom to which it is bound and the intermediate carbon atom, forms a heterocyclic group consisting of 5-8 ring atoms, in which, in addition to the nitrogen atom already present, a —CO—group or a second hetero atom from the group N, O,S, S—O or SO₂ may be present, which ring may be substituted with 1 to 3 $C_{1-4}$alkyl groups, a phenyl group or a $C_{2-5}$spiroalkyl group, or which ring may be annelated with a saturated or non-saturated carbocylic or heterocyclic ring which consists of 5- or 6- ring atoms and which may be substituted; m is 1 to 5; and $R_2$, $R_3$ and $R_4$ each represent a hydrogen atom or one of a variety of substituents.

U.S. Pat. No. 4,619,941 discloses indole carboxamides which may be represented by the general formula:

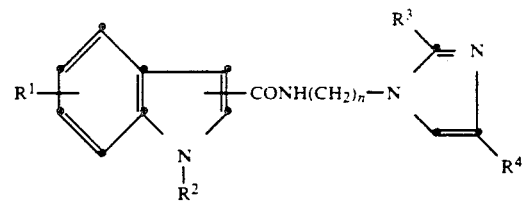

wherein $R^1$ represents a hydrogen or a halogen atom, or a $C_{1-3}$alkyl or $C_{1-3}$alkoxy group; $R^2$ represents a hydrogen atom or a $C_{1-3}$alkyl or benzyl group; n represents an integer from 2 to 8; and $R^3$ and $R^4$ independently represent a hydrogen atom, or a $C_{1-3}$alkyl or phenyl group.

However, these compounds are described in U.S. Pat. No. 4,619,941 as inhibitors of the enzyme thromboxane synthetase which are useful in the treatment of, for example, ischaemic heart disease.

We have now found a novel group of compounds which differ in structure from those described previously, and which are potent antagonists of the effect of 5-HT at 5-HT$_3$ receptors. The present invention provides an amide derivative of the general formula (I):

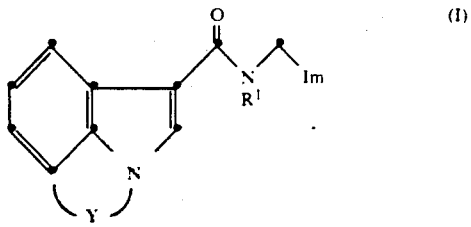

wherein R$^1$ is a hydrogen atom or a C$_{1-6}$alkyl group; Y represents a group —(CH$_2$)$_m$—, where m represents 2, 3 or 4 or a group —X(CH$_2$)$_p$, where p represents 2 or 3, X represents an oxygen or a sulphur atom or a group NR$^5$, where R$^5$ is a C$_{1-6}$alkyl group, and X is attached to the benzene ring moiety of the molecule; and Im represents an imidazolyl group of the formula:

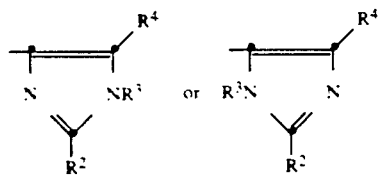

wherein one of the groups represented by R$^2$, R$^3$ and R$^4$ is a hydrogen atom or a C$_{1-6}$alkyl, C$_{3-7}$cycloalkyl, C$_{3-6}$alkenyl, phenyl or phenylC$_{1-3}$alkyl group, and each of the other two groups, which may be the same or different, represents a hydrogen atom or a C$_{1-6}$alkyl group; and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, propyl, prop-2-yl, butyl, but-2-yl, 2-methylprop-2-yl, pentyl, pent-3-yl or hexyl. A C$_{3-6}$alkenyl group may be, for example, a propenyl or butenyl group. When R$^2$ represents a C$_{3-6}$alkenyl group, the double bond may not be adjacent to the nitrogen atom. A phenylC$_{1-3}$alkyl group may be, for example, a benzyl, phenethyl or 3-phenylpropyl group. A C$_{3-7}$cycloalkyl group may be, for example, a cyclopropyl, cyclobutyl, cyclopentyl, cyclohexyl or cycloheptyl group.

A preferred class of compounds of formula (I) is that in which R$^2$, R$^3$ and R$^4$ each independently represent a hydrogen atom or a C$_{1-3}$alkyl (e.g. methyl) group. A further preferred class of compounds is that wherein R$^2$ and R$^3$ each represent a hydrogen atom, and R$^4$ is a C$_{1-3}$alkyl (e.g. methyl) group.

Another preferred class of compounds of formula (I) is that in which Y represents the group —(CH$_2$)$_3$—.

Another preferred class of compounds of formula (I) is that in which R$^1$ represents a C$_{1-3}$alkyl (e.g. methyl) group.

A preferred compound according to the invention is 5,6-dihydro-N-methyl-N-[(5-methyl-1H-imidazol-4-yl)methyl]-4H-pyrrolo[3,2,1-ij]quinoline-1-carboxamide and its physiologically acceptable salts and solvates.

The potent and selective antagonism of 5-HT at 5-HT$_3$ receptors by the compounds of the invention has been demonstrated by their ability to inhibit 3-(5-methyl-1H-imidazol-4-yl)-1-[1-(methyl-t$_3$)-1H-indol-3-yl[-1-propanone binding in rat entorhinal cortex homogenates (following the general procedure described by G. Kilpatrick et al in Nature, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia or another congitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hyrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents.

Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H^-K^-ATPase$ inhibitors (e.g. omeprazole). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I), and physiologically acceptable salts or solvates thereof, may be prepared by the general methods outlined hereinafter. In the following description, the groups $R^1$ to $R^4$, Y and Im are as previously defined for compounds of general formula (I) unless otherwise stated.

According to a first general process (A), a compound of general formula (I) may be prepared by reacting an acid of formula (II):

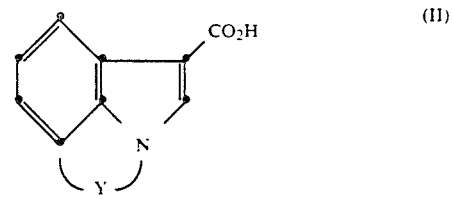

or an activated derivative thereof, with a compound of formula (III):

or a salt or protected derivative thereof, optionally in the presence of a base (e.g. triethylamine or N,N-diisopropylethylamine), followed where necessary by removal of any protecting groups.

Suitable activated derivatives of the acid (II) include acid halides (e.g. acid chlorides), anhydrides (e.g. symmetrical anhydrides or mixed anhydrides) and esters. When an activated derivative of the acid (II) is used the reaction may be conveniently effected in an inert solvent such as an ether (e.g. tetrahydrofuran), a halogenated hydrocarbon (e.g. dichloromethane or 1,2-dichloroethane) or a nitrile (e.g. acetonitrile) and at a temperature of, for example, $-10°$ to $+100°$ C.

Alternatively, a compound of general formula (I) may be prepared by the reaction of the free acid (II) with the amine (III) using standard coupling reagents for peptide synthesis (e.g. diphenylphosphoryl azide, dicyclohexylcarbodiimide or N,N'-carbonyldiimidazole). The reaction may be conveniently effected in an inert solvent and at a temperature as described above.

Activated derivatives corresponding to the acids of formula (II) may be prepared by conventional methods. Thus an acid halide may be prepared by reacting an acid (II) or a salt thereof with a halogenating reagent (e.g. oxalyl chloride or thionyl chloride).

Anhydrides may be prepared by reacting an acid (II) with an appropriate acid halide in the presence of a base, or alternatively by reacting an acid halide corresponding to the compound of formula (II) with an acid, in the presence of a base.

Esters may be prepared by reacting an acid halide or anhydride corresponding to the compound of formula (II) with an appropriate alcohol, optionally in the presence of a base (e.g. triethylamine or pyridine).

According to another general process (B), a compound of general formula (I) may be converted into another compound of formula (I) using conventional techniques. Such conventional techniques include hydrogenation and alkylation using protection and deprotection where necessary.

Thus, according to one embodiment of the interconversion process (B), hydrogenation may be used to convert an alkenyl substituent into an alkyl substituent. Hydrogenation according to general process (B) may be effected using conventional procedures, for example, using hydrogen in the presence of a catalyst, as described in published European Patent Specification No. 242973.

The term 'alkylation' according to general process (B) includes the introduction of groups such as cycloalkyl, alkenyl or phenalkyl groups.

Thus, for example, a compound of formula (I) in which $R^3$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^3$ represents a hydrogen atom, using conventional procedures, for example as described in published European Patent Specification No. 242973. Thus the reactions may be effected using an appropriate alkylating agent of formula $R^6Z$ (where $R^6$ is the group to be introduced and Z is a leaving atom or group), preferably in the presence of a base.

It should be appreciated that in the above transformations it may be necessary or desirable to protect any sensitive groups in the molecule of the compound in question to avoid undesirable side reactions. For example, it may be necessary to protect the imidazole nitrogen atom, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, a trityl group may be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis.

Compounds of formula (II) may be prepared, for example, by reacting a compound of formula (IV):

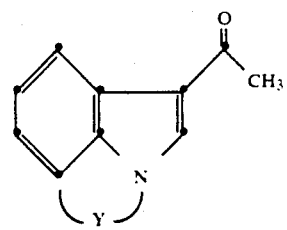

with a halogen (e.g. bromine, chlorine or iodine) and a base (e.g. sodium hydroxide), in a solvent such as aqueous dioxan.

Compounds of formula (IV) may be prepared, for example, by reaction of a compound of formula (V):

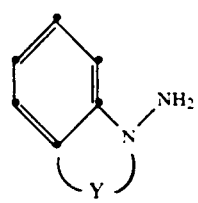

or a salt thereof, with a compound of formula (VI):

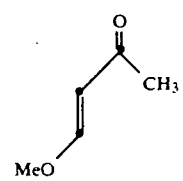

The cyclisation may be carried out in a solvent such as an alcohol (e.g. ethanol) in the presence of an acid catalyst such as an inorganic acid (e.g. concentrated hydrochloric acid) and at a temperature of from 20° to 125° C.

Compounds of formula (V) are either known, or may be prepared from known compounds by conventional procedures.

Compounds of formula (III) and protected derivatives thereof are either known, or may be prepared, for example, by the method described in published European Patent Specification No. 347229.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The various general methods described above may be used for the introduction of the desired groups at any stage in the stepwise formation of the required compound. and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Example. All temperatures are in °C. Thin layer chromatography (t.l.c.) was carried out on silica, and flash column chromatography (FCC) on silica (Merck 9385). Solvent System A as used for chromatography denotes dichloromethane:ethanol:0.88 ammonia solution. Organic extracts were dried, where indicated, over sodium sulphate or magnesium sulphate.

INTERMEDIATE 1

1-(5,6-Dihydro-4H-pyrrolo[3,2,1-ij]quinolin-1-yl)ethanone

A mixture of 1-amino-1,2,3,4-tetrahydroquinoline hemisulphate (8.05 g) and 4-methoxy-3-buten-2-one (4.2 ml) in ethanol (50 ml) and conc. hydrochloric acid (9.5 ml) was stirred at 20° for 1 h. The resulting solution was heated under reflux for 4.5 h. The mixture was cooled, concentrated to ca. 10 ml in vacuo and partitioned between ethyl acetate ($3 \times 150$ ml) and 1M hydrochloric acid (150 ml). The combined organic extracts were evaporated in vacuo to leave on oil (ca. 8 g) which was dissolved in dichloromethane (8 ml) and filtered through a small pad of FCC silica. This silica was then washed with dichloromethane (100 ml). The filtrates were combined and evaporated to leave an oil (ca. 6 g) which was purified by FCC eluting with hexane:ethanol:ammonia (400:100:1) to give an oil (3.5 g). This was crystallised from a mixture of ether:hexane (2:1; 50 ml) to give the title compound (2.2 g), m.p. 108°–110°.

INTERMEDIATE 2

5,6-Dihydro-4H-pyrrolo[3,2,1-ij]quinoline-1-carboxylic acid

A solution of sodium hydroxide (1.333 g) in water (10 ml) was cooled to $-5°$. Bromine (0.44 ml) was added to the solution over 5 min and the resulting mixture was diluted with dioxan (5 ml) and then added, with stirring, to a solution of 1-(5,6-dihydro-4H-pyrrolo[3,2,1-ij]-quinolin-1-yl)ethanone (0.511 g) in a mixture of water (10 ml) and dioxan (15 ml) at 0°. The resulting mixture was stirred at 0° for 6 h, and then at room temperature for 18 h. A solution of anhydrous sodium sulphite (0.645 g) in water (5 ml) was then added, and the aqueous solution was extracted with ether ($2 \times 50$ ml). The aqueous layer was then acidified with concentrated hydrochloric acid (3 ml) and extracted with ether ($3 \times 50$ ml). The latter combined ethereal extracts were dried and evaporated under reduced pressure to give a solid (0.156 g) which was purified by FCC eluting with dichloromethane:ethanol:glacial acetic acid (100:10:2) to give the title compound (0.033 g), t.l.c. (dichloromethane:ethanol:glacial acetic acid, 100:10:2) Rf 0.77.

EXAMPLE 5,6-Dihydro-N-methyl-N-[(5-methyl-1H-imidazol-4-yl)methyl]-4H-pyrrolo[3,2,1-ij]quinoline-1-carboxamide d,l -tartrate To a suspension of 5,6-dihydro-4H-pyrrolo[3,2,1-ij]quinoline-1-carboxylic acid (69 mg) in dry dichloromethane (5 ml) was added oxalyl chloride (2 ml), and the solution was stirred at room temperature under nitrogen overnight. The mixture was evaporated in vacuo and the residue was dissolved in dry dichloromethane (3 ml). To this solution was added N,5-dimethyl-1-(triphenylmethyl)-1H-imidazole-4-methanamine (151 mg), and the mixture was stirred at room temperature under nitrogen for 4 h. The solution was evaporated to dryness and the residue was suspended in dimethoxyethane (20 ml). Glacial acetic acid (3 ml) and water (3 ml) were added to this suspension, and the mixture was heated at reflux for 2 h. The solution was poured into 8% sodium bicarbonate solution (100 ml) and extracted with dichloromethane:ethanol (10:1) ($4 \times 100$ ml). The combined, dried organic extracts were evaporated under reduced pressure to give an oil (0.20 g) which was purified by FCC eluting with System A (100:15:1) to give the free base of the title compound as an oil (69.5 mg). This oil was dissolved in absolute ethanol (10 ml) and treated with a solution of anhydrous d,l -tartaric acid (36 mg) in absolute ethanol (5 ml). Ether (ca. 10 ml) was added and upon cooling the title compound crystallized out as a solid (18 mg). Further cooling gave another crop of the title compound (19 mg), t.l.c. (System A, 100:15:1) Rf 0.27.

Analysis Found: C, 57.4; H, 5.7; N,11.8; $C_{18}H_{20}N_4O.C_4H_6O_6.0.05\ H_2O$ requires C, 57.5; H, 5.7; N, 12.2%.

Water Analysis Found 0.19% w/w$\equiv$0.05 mol $H_2O$.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

Direct Compression Tablet

|  | mg/tablet |
| --- | --- |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm. flat bevelled edge punches.

INJECTION FOR INTRAVENOUS ADMINISTRATION

|  | mg/ml | |
| --- | --- | --- |
| Active ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under asptic conditions. The solution may be packed under an inert atmosphere of nitrogen or other suitable gas.

We claim:

1. A compound of formula (I)

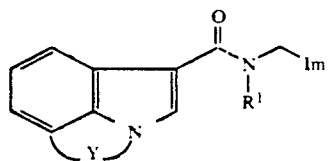

(I)

wherein $R^1$ is a hydrogen atom or a $C_{1-6}$alkyl group.

Y represents a group $—(CH_2)_m—$, where m represents 3; and

Im represents an imidazolyl group of the formula:

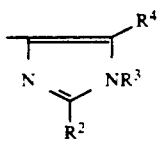

or

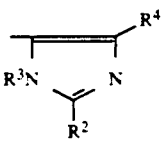

wherein one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group;

or a physiologically acceptable salt or solvate thereof.

2. A compound according to claim 1 in which $R^2$, $R^3$ and $R^4$ each independently represent a hydrogen atom or a $C_{1-3}$alkyl group.

3. A compound according to claim 1 in which $R^2$ and $R^3$ each represent a hydrogen atom, and $R^4$ is a $C_{1-3}$alkyl group.

4. A compound according to claim 1 in which $R^1$ represents a $C_{1-3}$alkyl group.

5. 5,6-Dihydro-N-methyl-N-[(5-methyl-1H-imidazol-4-yl)methyl]-4H-pyrrolo[3,2,1-ij]quinoline-1-carboxamide or a physiologically acceptable salt or solvate thereof.

6. A pharmaceutical composition which comprises an effective amount of a compound of formula (I) as defined in claim 1 or a physiologically acceptable salt or solvate thereof together with at least one pharmaceutically acceptable carrier or excipient.

7. A method of treating a condition which is ameliorated by the antagonism of 5-$HT_3$ receptors which comprises administering to a patient an effective amount to relieve said condition of a compound of formula (I) as defined in claim 1 or a physiologically acceptable salt or solvate thereof.

* * * * *